United States Patent
Bergstrom et al.

(10) Patent No.: US 8,574,437 B2
(45) Date of Patent: Nov. 5, 2013

(54) METHOD FOR PRODUCTION OF CHROMATOGRAPHY MEDIA

(75) Inventors: Jan Bergstrom, Balinge (SE); Bo-Lennart Johansson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/575,750

(22) PCT Filed: Feb. 16, 2011

(86) PCT No.: PCT/SE2011/050165
§ 371 (c)(1),
(2), (4) Date: Jul. 27, 2012

(87) PCT Pub. No.: WO2011/102790
PCT Pub. Date: Aug. 25, 2011

(65) Prior Publication Data
US 2012/0309618 A1    Dec. 6, 2012

(30) Foreign Application Priority Data
Feb. 19, 2010  (SE) ...................................... 1050157

(51) Int. Cl.
*B01D 15/08*    (2006.01)
(52) U.S. Cl.
USPC ..... 210/635; 210/656; 210/198.2; 210/502.1; 502/401; 502/439
(58) Field of Classification Search
USPC ............ 210/635, 656, 198.2, 502.1; 502/401, 502/402, 403, 404, 439
See application file for complete search history.

(56) References Cited

U.S. PATENT DOCUMENTS

| | | | |
|---|---|---|---|
| 5,110,784 A * | 5/1992 | Williams et al. | 502/401 |
| 5,135,650 A | 8/1992 | Hjerten et al. | |
| 6,428,707 B1 | 8/2002 | Berg et al. | |
| 6,572,766 B1 | 6/2003 | Bergstrom et al. | |
| 7,678,269 B2 * | 3/2010 | Cheng et al. | 210/198.2 |
| 2004/0050784 A1 * | 3/2004 | Belew et al. | 210/638 |
| 2004/0214157 A1 | 10/2004 | Burton et al. | |
| 2005/0242037 A1 * | 11/2005 | Berg et al. | 210/656 |
| 2006/0051583 A1 * | 3/2006 | Lau et al. | 428/407 |
| 2010/0032374 A1 * | 2/2010 | Powell et al. | 210/638 |
| 2011/0155668 A1 * | 6/2011 | Glad et al. | 210/656 |

FOREIGN PATENT DOCUMENTS

WO    WO 2009/131526    10/2009

OTHER PUBLICATIONS

Sluyterman, L., et al., Journal of Chromatography, vol. 206, No. 3, pp. 441-447.
Toribio, F., et al., Journal of Chromatography B, vol. 684, No. 1, 1996, pp. 1-23.

* cited by examiner

*Primary Examiner* — Ernest G Therkorn

(57) ABSTRACT

The present invention relates to a method of producing novel chromatography media and use thereof for purification of biomolecules, such as proteins. The chromatography media comprises shell beads having an inner porous core and an outer shell. The method comprises providing buffering ligands in the core of the beads, and providing binding ligands aimed for biomolecule binding in the outer shell of the beads. This method makes it possible to optimize binding properties and buffering properties independently of each other which is especially to advantageous for production of chromatofocusing media.

11 Claims, 3 Drawing Sheets

A shell functionalized with a strong IEX ligand and an optional surface extender for enhanced capacity Functionalized core with an optimized buffering capacity.

METHOD FOR PRODUCTION OF CHROMATOGRAPHY MEDIA

CROSS-REFERENCE TO RELATED APPLICATIONS

This application is a filing under 35 U.S.C. 371 of international application number PCT/SE2011/050165, filed Feb. 16, 2011, published on Aug. 25, 2011 as WO 2011/102790, which claims priority to application number 1050157-5 filed in Sweden on Feb. 19, 2010.

FIELD OF THE INVENTION

The present invention relates to a method of producing novel chromatography media and use thereof for chromatography techniques using immobilized buffering ligands for the control of the running pH, such as for chromatofocusing techniques.

BACKGROUND OF THE INVENTION

Chromatographic media normally used for chromatofocusing of biomolecules are substituted with a suitable buffering and binding ligands homogeneous substituted in the beads to accomplish the pH-gradient and the separation. Chromatofocusing (CF) combines the advantage of ion-exchange procedures with the high resolution of isoelectric focusing into a single simple to use "isocratic" chromatographic focusing procedure. During chromatofocusing, a weak ion-exchange column of suitable buffering capacity is equilibrated with a buffer that defines the upper pH (in the case of anion exchange CF media) of the separation pH gradient to follow. A second "focusing" buffer is then applied to elute bound proteins, roughly in the order of their isoelectric (PI) points. The pH of the focusing buffer is adjusted to a pH that defines the lower limit of the pH gradient. The pH gradient is formed inside the packed column during isocratic elution with a single focusing buffer; no external gradient forming device is required. The pH gradient is formed as the eluting buffer (i.e., focusing buffer) titrates the buffering weak ion exchange groups on the ion exchanger. Peak widths in the range of 0.02-0.05 pH units and samples containing several hundred milligrams of protein can be processed in a single step. Focusing of the protein band occurs because the velocity of the mobile phase is higher than the velocity at which the generated pH gradient is developed and moves through the column. Faster transport of analytes down the column to a region with a pH that promotes binding than the movement of the binding region it self.

Chromatofocusing is a powerful analytical tool for characterization of amphoteric substances, such as proteins and large protein aggregates as e.g. virus, as well as an effective preparative technique for high purity protein isolation. The beads used in chromatofocusing are normally weak anion exchangers or ion exchangers with both strong and weak IEX ligands (e.g. PBE94, Mono P and DEAE media from GE Healthcare Biosciences AB) where the different amine ligands participate both in the separation process and the generation of the pH gradient through out the whole beads. Even with its prominence in protein separation and purification technology, the technology has remained mostly unchanged from the pioneering work of Sluyterman et al (J. Chromatography 150 (1978) 17-44).

New chromatographic polishing media for chromatofocusing (CF) with significantly improved loading capacities compared to existing CF media and improved peak shapes should be welcomed in the chromatographic area.

SUMMARY OF THE INVENTION

The present invention provides shell beads which improve the performance of ion exchange chromatography, especially chromatofocusing. The shell beads have a core of pH gradient generating ligands whereas the ligands interacting with the sample (proteins) are situated in an outer shell. The main advantage with the construction is an increase in capacity compared with conventional chromatofusing media due to enhanced binding strength especially at high pH:es for anion exchange ligands and at low pH:es for cation exchange ligands. The capacity is further enhanced if the outer shell ligand is attached via an extender or spacer. In one preferred embodiment of the invention the porosity of the core is adjusted to exclude proteins.

Thus, the invention relates to a method for producing chromatography media comprising shell beads having an inner porous core and an outer shell, for chromatography techniques of biomolecules using immobilized buffering ligands in the core, comprising providing buffering ligands in the core of the beads aimed for pH stabilization (buffering) and pH gradient generation, and providing binding ligands aimed for biomolecule binding in the outer shell of the beads, wherein the buffering ligands and binding ligands are adjusted independently of each other. This method makes it possible to optimize binding properties and buffering properties separately of a chromatography media, preferably chromatofocusing media.

According to a preferred embodiment the porosity of the core prevents biomolecules above a certain size to penetrate into the core.

The chromatography beads of the invention have a diameter exceeding 5 μm, preferably a diameter between 5 to 400 μm.

Preferably, the outer shell is 0.5-30 μm thick. In some embodiments the outer shell is 0.5-5 μm. This thin outer layer is especially useful for applications in which fast kinetics are desired and is suitable for beads having a diameter of 3-200 μm. In other embodiments, the outer shell is 10-30 μm. This thicker outer layer is especially useful for applications in which it is desired to have a high loading capacity of the biomolecule to be separated. This thicker layer is suitable for beads having a diameter of 40-400 μm.

Preferably, the buffering ligands are weak acids and/or bases such as triethylenetetramine, bis(3-aminopropyl) amine, polyethyleneimine, mercaptoacetic acid, salicylic acid, polyacrylic acids, polyphosphonic acids and zwitterionic buffers.

Preferably, the binding ligands are strong anion exchange and/or strong cation exchange ligands such as quarternary amines, sulfonate ligands and guanidyl ligands. Any type of charged ligand for binding is suitable. It is important that the ligands bind strongly within the pH-interval used for the separation. In case of ion exchangers, this means that the ligand must be charged within the used pH-interval. For example, a diethyl amine-ligand is charged from pH 9-8 and below.

The binding ligands may also be affinity ligands, hydrophobic interaction (HIC, RPC) ligands, chelating ligands etc.

In a second aspect, the invention relates to a chromatography media produced according to the above mentioned methods.

In a third aspect, the invention relates to use of the above chromatography media comprising immobilized buffering ligands in the core (as buffer) instead of a buffer solution. The use may be for ion exchange chromatography but primarily for chromatofocusing. Chromatofocusing may be of any biomolecules for example selected from cells and/or parts thereof, virus and/or parts thereof, proteins, complexed proteins, fusion proteins, peptides, nucleic acids, amfoteric macromolecules and amfoteric particles. The method is suitable for all biomolecules having a pI between 2-13, preferably 3-11.

In one embodiment, elution buffer may, after finished chromatofocusing, be removed by running eluted fractions through a lid bead column, wherein biomolecules are excluded from the column and buffering components are adsorbed in the lid beads. This is described below in the experimental part.

This chromatofocusing (run with this type of media) has the same high separation power as isoelectric focusing and will find applications both in preparative and analytical areas.

DETAILED DESCRIPTION OF THE INVENTION

Figure 1:
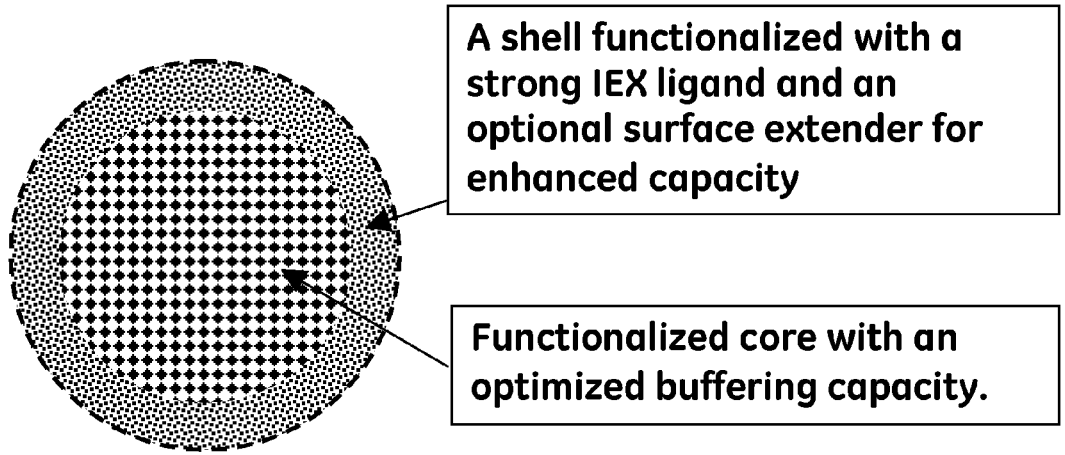
FIG. 1: Schematic view of a bead design for a new chromatography and chromatofocusing medium with separated regions for ligands primary involved in binding in the outer shell and buffering functional groups in the core.

The present inventors have found that shell beads where the ligands generating the pH gradient are attached in the core of the beads and the ligands interacting with the proteins are present in an outer shell (FIG. 1) are a much more optimal design of beads for chromatofocusing than conventional chromatofocusing media. By using layer functionalization it will be possible to have a high ligand density for binding without introducing an unnecessary high buffering capacity for gradient generation.

The main advantage with this idea is that the protein capacity is increased due to the possibility to use ligands whose binding properties are not changed by pH and to use higher ligand densities in the outer layer of the beads. This will enhance the binding strength without the introduction of an unnecessary high buffering capacity which is the case for traditional weak CF ion exchange ligands when the ligand density is raised. Weak ion exchanger ligands loses their charge and thus binding abilities at high or low pH:es depending on type. The loading capacity can also be adjusted by varying the thickness of the outer "shell". In addition, the capacity can be further improved if the "shell ligands" are attached via an extender. Furthermore, the shell can be made very thin (0.5-5 µm) which may improve the efficiency due to faster release kinetics resulting in shaper peaks.

By the separation of the binding and buffering regions in the beads one also reduces other peak broadening effects caused by secondary interactions as e.g hydrogen bonding.

In a preferred embodiment the porosity of the core is adjusted only to admit polybuffer components to have access to the interior of the beads. Consequently the proteins (in principal) only interact with the "shell ligands". The shell ligands will be designed to have none or very low buffer capacity in the pH-region of interest. This means that the most suitable shell ligands are Q (quaternary ammonium)-groups or SP (sulfopropyl)-groups.

Chromatofocusing has many potential applications in the field of proteomics, such as for the isolation and removal of major sample components to facilitate the analysis of low-abundance components, and for sample prefractionation prior to a subsequent separation using SDS-PAGE, narrow-pI-range 2D-PAGE, or additional chromatographic steps. However, the chromatofocusing techniques that are most commonly used with polyampholyte elution buffers which has limited the use of chromatofocusing in practice due to (buffer costs concerns and) concerns regarding the removal of ampholytes, such as Polybuffers™. Amphoteric buffers are designed to have an even buffercapacity and a high amount of components with isoelectric points in the pH interval they are supposed to be used in. Therefore this type of buffers will enhance the resolution in CF due to displacement and stacking effects that will cause spacing between bound proteins during the elution.

To expand the range of applications for this technique for cases where the highest possible resolution is not a priority the development of alternative buffer system may be an option.

Experimental Part

The present examples are presented herein for illustrative purpose only, and should not be constructed to limit the invention as defined by the appended claims.
General Volumes of matrix refer to settled bed volume and weights of matrix given in gram refer to suction dry weight. For reaction stirring is a motor-driven stirrer used since the use of magnet bar stirrer is prompt to damage the beads. Conventional methods were used for the analysis of the functionality and the determination of the degree of allylation, or the degree of amine content on the beads.

One way to prepare a separation matrix according to the invention is exemplified below, starting from a crosslinked agarose gel (Sepharose™ HFA 70, GE Healthcare, Uppsala, Sweden). The bead diameter of Sepharose HFA 70 is about 90 µm.

Preparation of Shell Media for Chromatofocusing
Based on Sepharose HFA 70-HFA 70 BAPA Shell-Q Allyl Activation of Sepharose HFA 70

Sepharose HFA 70 was washed with distilled water on a glass filter. The gel, 210 g drained gel, was weighed into a 3-necked round bottomed flask. NaOH (100 mL, 50%-solution) was added and mechanical stirring was started. Sodium borohydride, 0.5 g, and sodium sulphate, 31 g, were added to the flask and the slurry heated to 50° C. on a water bath. After approximately one hour, 20 mL of allyl glycidyl ether (AGE) was added. The slurry was then left under vigorously stirring over night. After about 20 hours the slurry was transferred to a glass filter and washed with distilled water (×4), ethanol (×4) and distilled water (×4).

The allyl content was then determined by titration; 152 µmol/mL.
Shell Activation (Partial Bromination)

Allylated gel, 50 mL, was weighed into a flask and 500 mL of distilled water and 2.5 g sodium acetate was added. 1.05 mL bromine (3.28 g) was dissolved in 197 mL distilled water and 38.5 mL of this solution was added to the allylated gel slurry. This amount of bromine is supposed to give (corresponds to) a shell thickness of about 2 μm. The bromine solution was momentary added to the allyl gel slurry during vigorous stirring. After approximately 10 minutes the gel was washed with distilled water on a glass filter.

Shell Coupling of the Q-Groups

The partially brominated gel (see above) was transferred to a flask and mixed with 20 mL of trimethylammonium chloride solution. pH was adjusted to 12 with 50% NaOH and the slurry was heated to 35° C. and left stirring over night. After approximately 18 hours the gel was washed with distilled water on a glass filter.

The chloride ion capacity was estimated to 50 μmol/mL. A residual allyl content of 90 μmol/mL corresponds to a theoretical shell thickness of ca 2 μm.

Coupling of BAPA (Bisaminopropylamine) in the Core of Beads 50 mL of "Q-shell gel (see above) was mixed with distilled water (50 mL) and 0.5 g sodium acetate in a beakers with overhead stirring. Bromine was added until the slurries had a remaining deeply orange/yellow colour. After 3 minutes of stirring, sodium formiate was added until the slurries were completely discoloured. The gels were then washed with distilled water on a glass filter.

40 mL of drained core brominated gel were transferred to a beaker and mixed with 10 mL of water, 10 mL bis-aminopropyl amine and 2 g of sodium sulphate. The mixtures were then stirred at 30° C. for 17 h, followed by washing with distilled water on a glass filter. The amount of bis-aminopropyl amine attached to the core of the gel was estimated to 80 μmol/mL.

Chromatographic Evaluation of a New CF-Prototype (HFA 70 BAPA Shell-Q) Compared to Mono P Introduction To test the behaviour of the shell CF media prototype (HFA 70 BAPA Shell-Q) the chromatograms of lens lectin and myoglobin were compared to the results obtained for Mono P (see the section Experimental). Mono P™ is an established medium based on 10-μm MonoBeads particles and is homogenously substituted with tertiary and quaternary amines. The small bead size contributes significantly to the high resolution that can be achieved. HFA 70 BAPA Shell-Q is based on a 90-μm agarose bead and according to established chromatographic theories the peak width should be much broader compare to Mono P. However, the comparison between the shell-prototype and Mono P illustrate the advantage of using beads as depicted in FIG. 1 compared to conventional beads of the same size.

Experimental

The shell medium to be investigated (HFA 70 BAPA Shell-Q), with respect to chromatographic performance, were packed in Tricorn 5/20 columns and the sample solution was pumped at a flow rate of 0.5 mL/min through the column after equilibration with buffer solution (25 mM diethanol amine, pH 9.3). The proteins were eluted by applying the buffer B (Polybuffer 96, pH6). The chromatographic method is depicted below (Unicorn method).

Sample

The sample was lens lectine and myoglobin dissolved in 25 mM diethanol amine, (pH 9.3) and the concentration was adjusted to 5.0 mg/ml. The sample volume was 100 μL.

Instrumental

LC System: Äkta Explore 10
Software: Unicorn
Column HR 5/20
Unicorn Method

Main Method:
0.0 Base CV (5) {ml} Any
0.00 Block Start_Conditions
   0.00 Base SameAsMain
   0.00 ColumnPosition (Position2)#colpos
   0.00 PumpAInlet A1
   0.00 AveragingTimeUV 2.56 {sec}
   0.00 Wavelength 280 {nm} 254 {nm} 215 {nm}
   0.00 BufferValveA1 A11
   0.00 Gradient 0.00 {%B} 0.00 {base}
   0.00 PumpBInlet B1
   0.00 Flow (0.50)#flow {ml/min}
   0.10 AutoZeroUV
   0.10 End_block
0.00 Block Column_Equilibration
   0.00 Base SameAsMain
   1.00 AutoZeroUV
   AutoZeroUV
   2.00 End_Block
0.00 Block Isocratic_Elution
   (Loading)
   0.00 Base SameAsMain
   0.00 AutoZeroUV
   0.00 InjectionValve Inject
   0.10 #injvol InjectionValve Load
   0.20 Gradient 100 {%B} 0 {base}
   8.00 Gradient 1000 {%B} 0 {base}
   9.00 End_Block New Method and Media for Efficient Removal of Buffer Substances After Chromatofocusing Polybuffer is composed of small molecules (<1000 g/mol) and can therefore easily be removed by a flow-through column packed with lid beads. These lid beads are designed with a gelfiltration lid (that excludes molecules larger than ca 5000-10000 g/mol) and a suitable ligand in the core (the choice depends on the polybuffer used) for adsorption of the polybuffer components. A slight change in pH of the sample solution is needed to change the net charge of the amphoteric buffer from zero to a for the adsorption suitable positive or negative value depending on which type of ligand that is used for the adsorption in the core of the lid bead.

Results and Discussion

To make improvements to the downstream chromatographic purification platform resulting in major increases to process productivity and protein manufacturing it is highly important to increase the chromatographic performance of media based on large beads (bead diameter larger than ca 40 μm). Media based on small beads (such as Mono P with a bead diameter of 10 mm) having the wanted selectivity does not allow high enough flow rates and productivity to be used in large scale columns within their pressure specification. This is the fact even for very rigid beads.

According to the present invention the efficiency (peak width) may be kept at the level of the small particle by using shell functionalized large particles.

Figure 2:
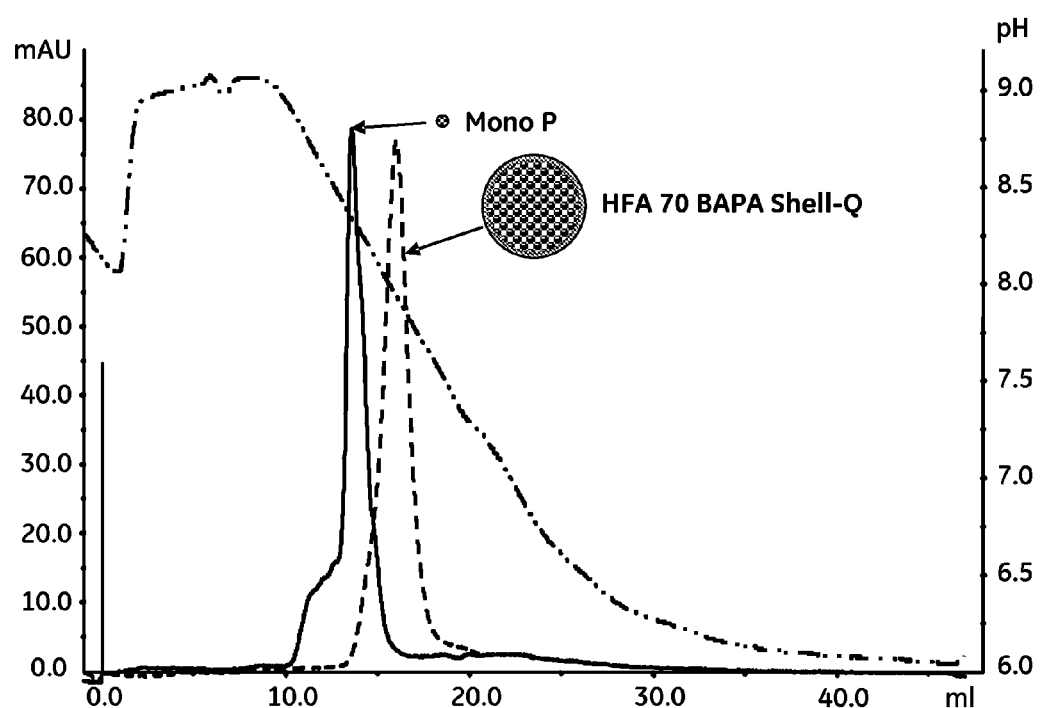
FIG. 2. Separation of lens lectine on conventional Mono P (bead diameter: 10 µm) and HFA 70 BAPA Shell-Q (bead diameter: 90 µm). The pH-gradient (—..—) was adjusted from 9 to 6.
Figure 3:
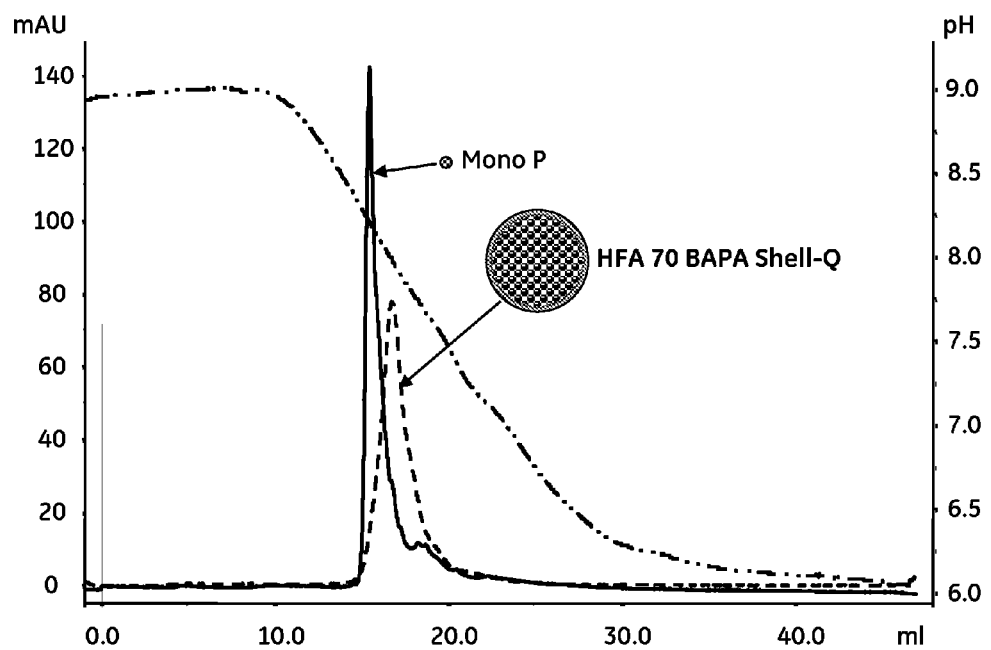
FIG. 3. Separation of Myoglobin on conventional Mono P (bead diameter: 10 µm) and HFA 70 BAPA Shell-Q (bead diameter: 90 µm). The pH-gradient (—..—) was adjusted from 9 to 6.

To prove the advantages of shell beads with large particle diameter (ca 90 μm) designed as depicted in FIG. 1 the chromatographic results were compared to "homogenous" bead (Mono P) with a particle size of 10 μm. According to FIGS. 2 and 3 the peak width/height was of the same size in case of lens lectine and slightly broader in case of myoglobin. The results clearly show that the larger shell beads designed as depicted in FIG. 1 are almost as good as the much smaller (10× smaller) conventional beads. The benefit of having large beads is that they are more suitable for larger scale preparative or process applications compared to small beads for use in analytical applications. With the new media design it is possible to combine demanded larger scale chromatography properties with and analytical properties as high efficiency.

The invention claimed is:

1. A method for producing chromatography media comprising shell beads having an inner porous core and an outer shell, for chromatography techniques of biomolecules using immobilized buffering ligands in the core, comprising providing buffering ligands in the core of the beads, and providing binding ligands in the outer shell of the beads, wherein the buffering ligands and binding ligands are adjusted independently of each other.

2. The method of claim 1 for production of chromatofocusing media.

3. The method of claim 1, wherein the porosity of the core prevents biomolecule to penetrate into the core.

4. The method of claim 1, wherein the beads have a diameter exceeding 3 μm.

5. The method of claim 4, wherein the beads have a diameter between 3 to 400 μm.

6. The method of claim 5, wherein the outer shell is 0.5-30 μm thick.

7. The method of claim 6, wherein the outer shell is 0.5-5 μm.

8. The method of claim 6, wherein the outer shell is 10-30 μm.

9. The method of claim 1, wherein the buffering ligands are weak acids and/or bases.

10. The method of claim 1, wherein the binding ligands are strong anion exchange and/or strong cation exchange ligands.

11. The method of claim 1, wherein the binding ligands are affinity ligands, hydrophobic interaction (HIC, RPC) ligands, or chelating ligands.

\* \* \* \* \*